(12) United States Patent
Lehmbeck

(10) Patent No.: US 7,063,962 B2
(45) Date of Patent: Jun. 20, 2006

(54) DNA SEQUENCES FOR REGULATING TRANSCRIPTION

(75) Inventor: Jan Lehmbeck, Vekso (DK)

(73) Assignee: Novozymes A/S, Bagsvaerd (DK)

( * ) Notice: Subject to any disclaimer, the term of this patent is extended or adjusted under 35 U.S.C. 154(b) by 43 days.

(21) Appl. No.: 10/194,550

(22) Filed: Jul. 12, 2002

(65) Prior Publication Data

US 2003/0087275 A1    May 8, 2003

Related U.S. Application Data

(60) Provisional application No. 60/307,240, filed on Jul. 23, 2001.

(30) Foreign Application Priority Data

Jul. 20, 2001  (DK) ................................ 2001 01132

(51) Int. Cl.
  *C12P 21/02*   (2006.01)
  *C12N 5/10*    (2006.01)
  *C12N 15/63*   (2006.01)
  *C12N 15/11*   (2006.01)

(52) U.S. Cl. .................. 435/69.1; 435/320.1; 435/325; 435/419; 536/24.1

(58) Field of Classification Search ............... 536/24.1; 435/320.1, 325, 419, 69.1
  See application file for complete search history.

(56) References Cited

U.S. PATENT DOCUMENTS

5,547,862 A * 8/1996 Meador et al. ............. 435/91.3
6,361,973 B1 * 3/2002 Berka et al. ............... 435/69.1

FOREIGN PATENT DOCUMENTS

| WO | WO 89/01969 | 3/1989 |
| WO | WO 99/43835 | 9/1999 |
| WO | WO 00/56900 | 9/2000 |

OTHER PUBLICATIONS

Song Ki-Bang et al, Korean Biochemistry Journal, vol. 20, Part 2, pp. 163-170, (1987).

* cited by examiner

*Primary Examiner*—Terry McKelvey
(74) *Attorney, Agent, or Firm*—Elias J. Lambiris

(57) ABSTRACT

The invention relates to a DNA sequences for regulating transcription of a structural gene encoding a polypeptide in a eukaryotic host cell comprising (a) a first DNA sequence to which RNA polymerase binds which DNA sequence comprises a mRNA initiation site; and further (b) one or more DNA sequence(s) to which RNA polymerase binds with or without a mRNA initiation site. The invention also relates to a DNA construct and an expression vector and a host cell comprising the DNA sequence of the invention.

23 Claims, 2 Drawing Sheets

US 7,063,962 B2

SEQUENCE LISTING

<160> NUMBER OF SEQ ID NOS: 24

<210> SEQ ID NO 1
<211> LENGTH: 617
<212> TYPE: DNA
<213> ORGANISM: Aspergillus niger
<220> FEATURE:
<221> NAME/KEY: promoter
<222> LOCATION: (1)..(617)
<223> OTHER INFORMATION: Pna2-tpi promoter

<400> SEQUENCE: 1

```
gaattcatgg tgttttgatc attttaaatt tttatatggc gggtggtggg caactcgctt      60
gcgcgggcaa ctcgcttacc gattacgtta gggctgatat ttacgtaaaa atcgtcaagg     120
gatgcaagac caaagtacta aaaccccgga gtcaacagca tccaagccca agtccttcac     180
ggagaaaccc cagcgtccac atcacgagcg aaggaccacc tctaggcatc ggacgcacca     240
tccaattaga agcagcaaag cgaaacagcc caagaaaaag gtcggcccgt cggccttttc     300
tgcaacgctg atcacgggca gcgatccaac caacaccctc cagagtgact aggggcggaa     360
atttatcggg attaatttcc actcaaccac aaatcacagt cgtccccggt attgtcctgc     420
agaatgcaat ttaaactctt ctgcgaatcg cttggattcc ccgcccctgg ccgtagagct     480
taaagtatgt cccttgtcga tgcgatgtat cacaacatat aaatactagc aagggatgcc     540
atgcttggag gatagcaacc gacaacatca catcaagctc tcccttctct gaacaataaa     600
ccccacagaa gggatcc                                                    617
```

<210> SEQ ID NO 2
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(29)
<223> OTHER INFORMATION: Primer

<400> SEQUENCE: 2

```
ggaacgatgg acccggaagg tttaaaagc                                        29
```

<210> SEQ ID NO 3
<211> LENGTH: 11
<212> TYPE: DNA
<213> ORGANISM: A. Niger
<220> FEATURE:
<221> NAME/KEY: misc_feature
<222> LOCATION: (1)..(11)
<223> OTHER INFORMATION: Nucleotide 135 - 145

<400> SEQUENCE: 3

```
gtactaaaac c                                                           11
```

<210> SEQ ID NO 4
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Nucleotide 135 - 145

```
<400> SEQUENCE: 4
ccgttaaatt t                                                    11

<210> SEQ ID NO 5
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(45)
<223> OTHER INFORMATION: Primer

<400> SEQUENCE: 5
ggatgctgtt gactccggaa atttaacggt ttggtcttgc atccc               45

<210> SEQ ID NO 6
<211> LENGTH: 16
<212> TYPE: DNA
<213> ORGANISM: A. Niger
<220> FEATURE:
<221> NAME/KEY: misc_feature
<222> LOCATION: (1)..(16)
<223> OTHER INFORMATION: Nucleotide 407 - 422

<400> SEQUENCE: 6
cggtattgtc ctgcag                                               16

<210> SEQ ID NO 7
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: Nucleotide 407 - 422

<400> SEQUENCE: 7
cggtaattta acggctgcag                                           20

<210> SEQ ID NO 8
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(36)
<223> OTHER INFORMATION: Primer

<400> SEQUENCE: 8
ccgtctgcag ccgttaaatt accggggacg actgtg                         36

<210> SEQ ID NO 9
<211> LENGTH: 14
<212> TYPE: DNA
<213> ORGANISM: A. Niger
<220> FEATURE:
<221> NAME/KEY: misc_feature
<222> LOCATION: (1)..(14)
<223> OTHER INFORMATION: Nucleotide 424 - 437

<400> SEQUENCE: 9
```
atgcaattta aact                                                        14

<210> SEQ ID NO 10
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(16)
<223> OTHER INFORMATION: Nucleotide 424 - 437

<400> SEQUENCE: 10
cggcaattta acgg                                                        14

<210> SEQ ID NO 11
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(44)
<223> OTHER INFORMATION: Primer

<400> SEQUENCE: 11
ggtattgtcc tgcagacggc aatttaacgg cttctgcgaa tcgc                        44

<210> SEQ ID NO 12
<211> LENGTH: 60
<212> TYPE: DNA
<213> ORGANISM: A. Niger
<220> FEATURE:
<221> NAME/KEY: misc_feature
<222> LOCATION: (1)..(65)
<223> OTHER INFORMATION: Nucleotide 529 - 617

<400> SEQUENCE: 12
gatagcaacc gacaacatca catcaagctc tcccttctct gaacaataaa ccccacagaa       60

<210> SEQ ID NO 13
<211> LENGTH: 65
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(65)
<223> OTHER INFORMATION: Nucleotide 529 - 617

<400> SEQUENCE: 13
tttccaactc aatttacctc tatccacact tctcttcctt cctcaatcct ctatatacac       60
aactg                                                                  65

<210> SEQ ID NO 14
<211> LENGTH: 106
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(106)
<223> OTHER INFORMATION: Primer

<400> SEQUENCE: 14
gctcctcatg gtggatcccc agttgtgtat atagaggatt gaggaaggaa gagaagtgtg    60
gatagaggta aattgagttg gaaactccaa gcatggcatc ccttgc    106

<210> SEQ ID NO 15
<211> LENGTH: 37
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(37)
<223> OTHER INFORMATION: Primer

<400> SEQUENCE: 15
gacgacgaat tcaagcttat ggtgttttga tcattttt    37

<210> SEQ ID NO 16
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(31)
<223> OTHER INFORMATION: Primer

<400> SEQUENCE: 16
gacgacgaat tcatacatcg catcgacaag g    31

<210> SEQ ID NO 17
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(31)
<223> OTHER INFORMATION: Primer

<400> SEQUENCE: 17
gacgacgaat tcatacatcg catcgacaag g    31

<210> SEQ ID NO 18
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(32)
<223> OTHER INFORMATION: Primer BgIIIaccPME

<400> SEQUENCE: 18
atagatctac catggttaag tcaattcttg ca    32

<210> SEQ ID NO 19
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(32)

<223> OTHER INFORMATION: Primer XhoPME

<400> SEQUENCE: 19
atctcgagac cgcttacaac tttcacacaa gt					32

<210> SEQ ID NO 20
<211> LENGTH: 68
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(68)
<223> OTHER INFORMATION: Primer rika1

<400> SEQUENCE: 20
aaatactggc aagggatgcc atgcttggag gatagcaacc gacaacatca catcaagctc		60 tcccttct									68

<210> SEQ ID NO 21
<211> LENGTH: 69
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(69)
<223> OTHER INFORMATION: Primer rika2

<400> SEQUENCE: 21
atggatccct tctgtggggt ttattgttca gagaagggag agcttgatgt gatgttgtcg		60 gttgctatc									69

<210> SEQ ID NO 22
<211> LENGTH: 37
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(37)
<223> OTHER INFORMATION: Primer rika4

<400> SEQUENCE: 22
atgaattcat ggtgttttga tcattttaaa tttttat				37

<210> SEQ ID NO 23
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: Primer NA2F

<400> SEQUENCE: 23
tttcaattga agcttatggt gttttgat						28

<210> SEQ ID NO 24
<211> LENGTH: 28
<212> TYPE: DNA
<213> ORGANISM: Artificial Sequence

```
<220> FEATURE:
<223> OTHER INFORMATION: Primer
<220> FEATURE:
<221> NAME/KEY: misc_feature
<222> LOCATION: (1)..(28)
<223> OTHER INFORMATION: Primer NZ2R

<400> SEQUENCE: 24
tttgaattca tacatcgcat cgacaagg                                              28
```

DNA SEQUENCES FOR REGULATING TRANSCRIPTION

CROSS-REFERENCE TO RELATED APPLICATIONS

This application claims, under 35 U.S.C. 119, priority or the benefit of Danish application no. PA 2001 01132 filed Jul. 20, 2001 and U.S. provisional application No. 60/307,240 filed Jul. 23, 2001, the contents of which are fully incorporated herein by reference.

FIELD OF THE INVENTION

The present invention relates to a control element for increasing transcription of a structural gene in eukaryotic organisms in connection with homologous and heterologous production of polypeptides.

BACKGROUND OF THE INVENTION

Eukaryotic organisms are widely used in industry as host cells for producing polypeptide for, e.g., pharmaceutical and industrial applications. The ability to manipulate gene transcription and expression gives the basis for providing higher production yields.

Conventionally, maximal expression of a gene in a eukaryotic organism is achieved by amplifying in the chromosome an expression cassette containing a single promoter operably linked to a gene encoding the polypeptide of interest and an amplifier selective marker.

Upstream from a structural gene encoding a polypeptide of interest there is a DNA sequence region (normally referred to as the promoter region) to which RNA polymerase binds. The RNA polymerase catalyses the assembly of the mRNA complementary to the appropriate DNA strand of the polypeptide coding region. Most "promoter regions" comprise a RNA polymerase recognition site (often a TATA box) located upstream from the start of the coding region (structural gene) and the site for accurate initiation of transcription.

Modification in the "promoter region" may result in enhanced transcription levels, which again may lead to increased expression and production yields.

SUMMARY OF THE INVENTION

The present invention relates to DNA sequences that regulates the transcription level of eukaryotic host cells, in particular fungal organisms, especially filamentous fungi, in comparison to the corresponding parent eukaryotic host cell, so that the transcription and/or expression levels are increased.

Definitions

The terms "DNA sequence" and "nucleic acids sequence" are used interchangeably below.

The term "operably linked" is defined herein as a configuration in which, e.g., a DNA sequence of the invention is appropriately placed at a position relative to a polypeptide coding DNA sequence such that increased transcription levels are obtained.

"Coding sequence" is defined herein as a nucleic acid or DNA sequence, which is transcribed into mRNA and translated into a polypeptide when placed under the control of the appropriate control sequences. The boundaries of the coding sequence are generally determined by a ribosome binding site located just upstream of the open reading frame at the 5' end of the mRNA and a transcription terminator sequence located just downstream of the open reading frame at the 3' end of the mRNA. A coding sequence can include, but is not limited to, genomic DNA, cDNA, semi-synthetic, synthetic, and recombinant nucleic acid sequences.

"Nucleic acid construct" or "DNA construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the controlling sequences required for expression of a coding sequence.

A "RNA polymerase" is 1) able to recognize a promoter or the like controlling elements in the double stranded state of DNA; 2) is able to "burrow into" the DNA duplex at the proper promoter region and unwind the initiation site of the gene for transcription; 3) copy the gene; 4) stops transcription when it encounters and recognizes terminator sequence. In eukaryotes three RNA polymerises are known and referred to RNA polymerase I, II, and III. In context of the present invention RNA polymerase II is the most relevant.

That two RNA polymerase binding sites or promoters are "closely linked" or "in proximity" means that no or only few base pairs separate the 5' end of the first RNA polymerase binding site or promoter and the adjacent 3' end of the second RNA polymerase binding site or promoter. In an embodiment of the invention there may be from 0 to 100 bp in between the two RNA polymerase binding sites or promoters. This also applies to the spacing between the second and third RNA polymerase binding sites or promoters and the third and forth RNA polymerase binding sites or promoters etc.

The term "terminator" means the site where transcription is concluded.

"Transcription factor": Many transcription factors are regulatory proteins that respond to stimuli to the cell (e.g., addition of a carbohydrate) by binding to the TATA box (RNA polymerase recognition site) resulting in either activation or repressing of the transcription.

The "Transcription factor binding site" is the DNA site where the Transcription factor binds.

The term "homologous" or "recombinant" expression or production means in the context of the present invention that the polypeptide in question is expressed from a gene endogenous to the donor cell or that a DNA construct comprising the gene encoding the polypeptide in question is introduced into the donor cell and expressed from this genetically modified donor cell.

The term "donor cell" means the cell from which the gene encoding the polypeptide is obtained.

DETAILED DESCRIPTION OF THE INVENTION

Figure 1:
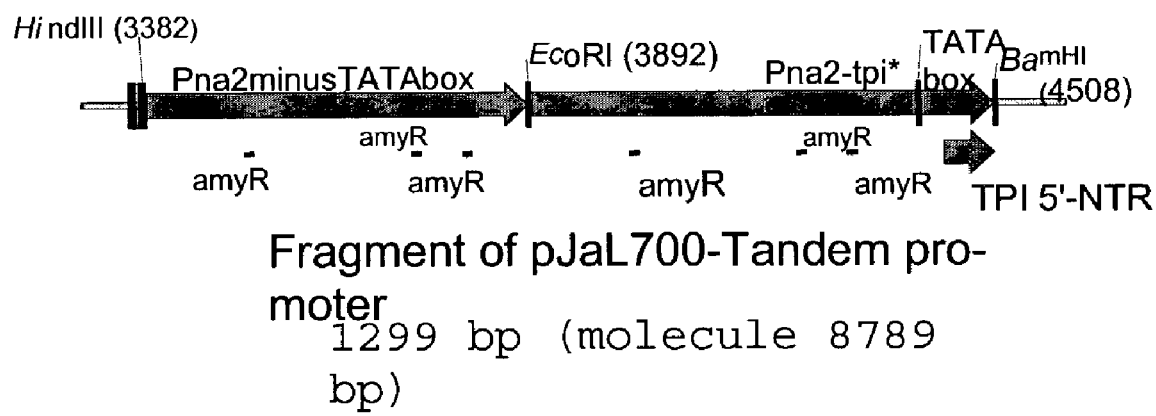
FIG. 1 shows a restriction map of pJaL700.

The present invention relates to DNA sequences that regulate the transcription levels of eukaryotic host cells, in particular fungal organisms, especially filamentous fungi, in comparison to the corresponding parent eukaryotic host cells, so that the transcription and/or expression levels are increased.

A DNA sequence of the invention comprises at one or more RNA polymerase binding sites or regions and one or more mRNA initiation sites. The DNA sequence of the invention may comprise a part of or the whole of one, two, three or more RNA polymerase binding sites or promoters.

A DNA sequence of the invention may further comprise one or more RNA polymerase recognition sites, in particular a TATA box or the like.

Thus, in the first aspect the invention relates to a DNA sequence for regulating transcription of a structural gene encoding a polypeptide in a eukaryotic host cell comprising:

(a) a first DNA sequence to which RNA polymerase binds which DNA sequence comprises a mRNA initiation site; and (b) one or more DNA sequence(s) to which RNA polymerase binds with or without (a) mRNA initiation site(s).

In one embodiment a second DNA sequence as defined under (b) may have a RNA binding region that is substantially identical to the RNA binding region defined under (a). Thus, the RNA polymerase binding sites may in an embodiment be tandem sites or repetitive sites. In a preferred embodiment the two or more RNA binding sites (regions) each are constituted by a part of or the whole of one or more promoter sequences. The RNA binding site of a promoter comprises at least the part required for RNA polymerase binding.

The DNA sequence of the invention normally also includes a RNA polymerase recognition site. This may be a TATA box or the like. However, examples of, e.g., eukaryotic promoters without a TATA box is known. In an embodiment only the RNA binding site closest to the structural gene encoding a polypeptide has a RNA polymerase recognition site. Said recognition site may be upstream to the structural gene, but downstream to the second, third or more RNA binding site.

The DNA sequence of the invention may comprise a third DNA sequence to which RNA polymerase binds. This site or region may in an embodiment be the whole of a promoter without the mRNA initiation site and may also be without a RNA polymerase recognition site. In another embodiment the third DNA sequence to which the RNA polymerase binds may include a region comprising a RNA polymerase recognition site and/or mRNA initiation site. In a preferred embodiment the RNA polymerase binding site is the whole or a functional part of the NA2-tpi promoter shown in SEQ ID NO: 1 or the whole or a functional part of the NA2 promoter shown in positions 1 to 510 of SEQ ID NO: 1 or positions 7 to 510 of SEQ ID NO: 1. The second, third or more DNA sequence defined in (b) may preferably be the whole or a functional part of the NA2-tpi promoter shown in SEQ ID NO: 1 with or without a RNA polymerase recognition site and/or mRNA initiation site or the whole or a functional part of the NA2 promoter shown in positions 1 to 510 of SEQ ID NO: 1 or positions 7 to 510 of SEQ ID NO: 1, with or without a RNA polymerase recognition site and/or mRNA initiation site.

In a preferred embodiment of the invention the 3' end(s) of the second, third and/or more RNA polymerase binding sites are located upstream to the 5' end of the first RNA polymerase binding site, which is located upstream to the structural gene encoding a polypeptide. Further, in a preferred embodiment the of the invention the third RNA polymerase binding site is located upstream to the 5' end of the second RNA polymerase binding site, which is located upstream to the first RNA polymerase binding site which is located upstream to the structural gene encoding a polypeptide. It is within the scope of the invention that one or more of the DNA sequences defined under (b) comprises an mRNA initiation site and/or RNA polymerase recognition site.

According to the invention the DNA sequence of the invention for regulating transcription may comprise two or more repetitive RNA polymerase binding sites, in particular 2–5. In an embodiment the RNA polymerase sites are located in tandem or are closely and operably linked to each other. The RNA binding sites should be located so that their function has an impact on the overall transcription level or expression level. This may be tested by comparing the transcription or expression levels obtained in comparison to the transcription level of a corresponding parent eukaryotic host cell which only comprises a DNA sequence or promoter as defined under (a) above.

In a preferred embodiment the DNA sequence of the invention for regulating transcription comprises two or three RNA polymerase binding sites where only the (first) RNA polymerase binding site closest to the structural gene encoding a polypeptide has an mRNA initiation site and optionally a RNA polymerase recognition site.

According to the invention the DNA sequence of the invention may comprise one or more transcription factor binding sites. In an embodiment the transcription factor binding site(s) is(are) located upstream to the first RNA polymerase recognition site and/or mRNA initiation site. In a preferred embodiment the transcription factor binding site is an *Aspergillus* transcription factor binding site, such as a transcription factor binding site derived from *A. niger*, *A. nidulans* or *A. oryzae*, in particular an *Aspergillus* amyR binding site described in WO 98/01470 (which is hereby incorporated by reference).

The RNA polymerase binding site may as mentioned above be a promoter, in particular a promoter selected from the group consisting of the *A. oryzae* TAKA amylase, NA2-tpi (a hybrid of the promoters from the genes encoding *Aspergillus niger* neutral alpha-amylase and *Aspergillus oryzae* triose phosphate isomerase), and glaA promoters or as described below.

In a preferred embodiment of the DNA sequence of the invention the second RNA polymerase binding site is located upstream relative to the 5' end of the first RNA polymerase binding site which includes a mRNA initiation site. In an embodiment the sites are closely linked. This include that the sites may be separated by from 0 to 100 bp of each other, in particular 10–50 bp of each other, especially in 4–30 bp of each other.

The parts constituting the DNA sequence of the invention or the whole DNA sequence of the invention may be artificial or may be derived from a eukaryotic organism, in particular a filamentous fungi, in particular a strain of the genus *Aspergillus, Trichoderma, Fusarium* or any of the eukaryotic organisms described below in the "Eukaryotic Host Cell"-section.

The structural gene may encode any polypeptide. In an embodiment the structural gene encodes a polypeptide with a biological activity. In a preferred embodiment the structural gene encodes a polypeptide exhibiting enzymatic activity, in particular an enzyme activity selected from the group consisting of an oxidoreductase, transferase, hydrolase, lyase, isomerase, or ligase, such as an enzyme selected from the group consisting of aminopeptidase, alpha or beta or maltogenic amylase, CGTase, mannanase, carbohydrase, carboxypeptidase, catalase, cellulase, chitinase, cutinase, deoxyribonuclease, dextranase, esterase, alpha-galactosidase, beta-galactosidase, glucoamylase, alpha-glucosidase, beta-glucosidase, haloperoxidase, invertase, laccase, lipase, mannosidase, mutanase, oxidase, pectin methyl esterase, pectinolytic enzyme, such as pectate lyase, pectin esterase, peroxidase, phytase, polyphenoloxidase, proteolytic enzymes, such as proteases or peptidases, ribonuclease, transglutaminase, or xylanase.

The invention also relates to a DNA construct comprising a DNA sequence of the invention for regulating transcription. The DNA construct of the invention is operative in a eukaryotic host cell as defined below and the DNA sequences of the invention are operable linked with a structural gene encoding a polypeptide and a terminator. The DNA construct may further comprise the below control sequences.

The invention also relates to an expression vector comprising a DNA construct of the invention. The DNA construct may further comprise a signal peptide coding region. In such embodiment the transcribed and expression polypeptide will be secreted, in particular into the culture medium. An expression vector of the invention may comprise a DNA construct of the invention wherein the DNA sequence of the invention is operably linked to a single copy of a structural gene encoding a polypeptide, and optionally leader sequence located upstream of the structural gene encoding the polypeptide.

Control Sequences

As mentioned above a DNA construct of the invention may further comprise a control sequences. The DNA sequence of the invention may be considered a control sequence and may function as a promoter and may comprise one or more promoters.

A DNA sequence of the invention for regulating transcription contains transcription and translation control sequences, which mediate the expression of a polypeptide. The DNA sequence of the invention may comprise a promoter, a mutant thereof, or a truncated promoter or a hybrid promoter. The promoter may be any nucleic acid sequence, which shows transcriptional activity in a eukaryotic host cell of choice and may be obtained from genes encoding extracellular or intracellular polypeptides either homologous or heterologous to the host cell. Each promoter sequence may be native or foreign to the nucleic acid sequence encoding the polypeptide (structural gene) and native or foreign to the eukaryotic host cell in question. Each control sequence may be native or foreign to structural gene encoding the polypeptide in question to the transcribed and expression.

Such control sequences include, but are not limited to, a leader, a polyadenylation sequence, a propeptide sequence, a promoter or part thereof, a signal sequence, and a transcription terminator. The control sequences may be provided with linkers for the purpose of introducing specific restriction sites facilitating ligation of a nucleic acid sequence encoding the polypeptide in question which is operably linked to a control element of the invention.

Eukaryotic Promoters

The DNA sequence of the invention for regulating transcription may comprise a promoter sequence, which contains transcription and translation control sequences, which mediate the expression of a polypeptide. A promoter may be any nucleic acid sequence.

Eukaryotic promoters are DNA sequences providing gene expression regulation at the stage of transcription initiation and may be obtained from genes encoding extracellular or intracellular polypeptides either homologous or heterologous to the host cell in question.

Promoters have a complex block-modular structure and contain numerous short functional elements such as a transcription factor binding site, a RNA polymerase recognition site, a mRNA initiation site. These sequences have no exact uniform location and are dispersed in the 5'-flanking region up to about 1 kb upstream of the mRNA initiation site where transcription starts.

The DNA sequence of the invention, which encompasses at least one RNA polymerase binding site including at least one mRNA initiation site may comprise a RNA polymerase recognition site that directs the RNA polymerase to the mRNA initiation site. Belonging to these recognition sites are the TATA box with the consensus sequence TATA(A/T)A(A/T) and Inr with the consensus sequence YYAN(T/A)YY. Transcription initiation begins with formation of the basal transcription complex in the RNA polymerase binding region. In turn, assembling of the basal transcription complex at TATA-containing regions/promoters starts with the recognition of TATA boxes by TATA-binding protein (TBP).

TATA-box

The TATA box or the like, which may be comprised in the DNA sequence for regulating transcription of the invention can be found in various species ranging from simple eukaryotes such as baker's yeast to more complex organisms such filamentous fungi and humans. The TATA box assists in directing RNA polymerase (RNA polymerase 11) to the downstream mRNA initiation site. The RNA polymerase binds to regions of DNA, i.e., the RNA polymarase binding site often in general referred to as a promoter. The TATA box is in most cases necessary for transcription because the RNA polymerase normally cannot recognize the initiation sites on its own. The TATA box directs the RNA polymerase to the m RNA initiation site once the RNA polymerase has bound to the TATA box. Yet another problem occurs when the RNA polymerase scans for the TATA box. The RNA polymerase cannot recognize the TATA box on its own. It has to use (a) transcription factor(s) to find the TATA box. After the transcription factor(s) bind(s) to the TATA box, then the RNA polymerase can recognize and bind to the TATA box. Then the RNA polymerase binds to the transcription factor(s), which identify the TATA box. The TATA box then guides the RNA polymerase to the mRNA initiation site where transcription can begin.

Translation Regulator

The DNA sequence of the invention for regulating transcription may further comprise one or more translation regulating sequences. The translation regulator or leader sequence may be located downstream from the first RNA polymerase binding site, in particular downstream to the mRNA initiation site and upstream to the structural gene encoding a polypeptide. A suitable leader sequence or translation regulating sequence may be the triose phosphate isomerase gene (tpi) from *Aspergillus nidulans* or other *Aspergillus*.

Filamentous Fungi Promoters

Examples of promoters in filamentous fungal host cells are promoters obtained from the genes encoding *Aspergillus oryzae* TAKA amylase (EP238023), *Rhizomucor miehei* aspartic proteinase, *Aspergillus niger* neutral alpha-amylase (EP383779), *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288, 627, which is incorporated herein by reference), and hybrids thereof. Particularly preferred promoters for use in filamentous fungal host cells are the TAKA amylase, NA2, NA2-tpi (a hybrid of the promoters from the genes encoding *Aspergillus niger* neutral alpha-amylase and *Aspergillus oryzae* triose phosphate isomerase (tpi)), and glaA promoters.

Yeast Promoters

Examples of promotes in yeast host cells are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8:423–488.

Transcription Terminators

As mentioned above a DNA construct of the invention comprises a transcription terminator sequence, which is a sequence recognized by a host cell to terminate transcription. The terminator sequence is operably linked to the 3' terminus of the structural gene encoding a polypeptide. Any terminator, which is functional in the host cell of choice, may be used in the present invention.

Fungus Terminators

Examples of terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Yeast Terminators

Examples of terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al, 1992, *Yeast* 8:423–488. Terminator sequences are well known in the art for mammalian host cells.

Leader Sequences

The DNA construct of the invention may comprise a suitable leader sequence, a non-translated region of mRNA, which is important for translation by the host cell. The leader sequence is operably linked to the 5' terminus of the structural gene encoding a polypeptide. Any leader sequence, which is functional in the host cell of choice, may be used in the present invention.

Fungus Leader Sequences

Preferred leaders for filamentous fungal host cells are obtained from the genes encoding *Aspergillus oryzae* TAKA amylase and *Aspergillus oryzae* triose phosphate isomerase (tpi).

Yeast Leader Sequences

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

Polyadenylation Sequences

The DNA construct of the invention may also comprise a polyadenylation sequence, a sequence which is operably linked to the 3' terminus of the structural gene encoding the polypeptide and which, when transcribed, is recognized by the host cell as a signal to add polyadenosine residues to transcribed mRNA. Any polyadenylation sequence, which is functional in the host cell of choice, may be used in the present invention.

Fungus Polyadenylation Sequences

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Yeast Polyadenylation Sequences

Useful polyadenylation sequences for yeast host cells are described by Guo and Sherman, 1995, *Molecular Cellular Biology* 15:5983–5990. Polyadenylation sequences are well known in the art for mammalian host cells.

Signal Peptide

The DNA construct of the invention may comprise a signal peptide-coding region, which codes for an amino acid sequence linked to the amino terminus of the polypeptide, which can direct the expressed protein into the cell's secretory pathway. The 5' end of the coding sequence of the structural gene may inherently contain a signal peptide-coding region naturally linked in translation reading frame with the segment of the coding region, which encodes the secreted protein. Alternatively, the 5' end of the coding sequence may contain a signal peptide-coding region, which is foreign to that portion of the coding sequence, which encodes the secreted protein. The foreign signal peptide-coding region may be required where the coding sequence does not normally contain a signal peptide-coding region. Alternatively, the foreign signal peptide-coding region may simply replace the natural signal peptide-coding region in order to obtain enhanced secretion of the protein(s) relative to the natural signal peptide-coding region normally associated with the coding sequence. The signal peptide-coding region may be obtained from a glucoamylase or an amylase gene from an *Aspergillus* species, a lipase or proteinase gene from a Rhizomucor species, the gene for the alpha-factor from *Saccharomyces cerevisiae*, an amylase or a protease gene from a *Bacillus* species, or the calf preprochymosin gene. However, any signal peptide-coding region capable of directing the expressed protein into the secretory pathway of a host cell of choice may be used in the present invention.

Fungus Signal Peptide Sequences

An effective signal peptide coding region for filamentous fungal host cells is the signal peptide coding region obtained from *Aspergillus oryzae* TAKA amylase gene, *Aspergillus niger* neutral amylase gene, the *Rhizomucor miehei* aspartic proteinase gene, the *Humicola lanuginosa* cellulase gene, or the *Rhizomucor miehei* lipase gene.

Yeast Signal Peptide Sequences

Useful signal peptides for yeast host cells are obtained from the genes for *Saccharomyces cerevisiae* alpha-factor and *Saccharomyces cerevisiae* invertase. Other useful signal peptide coding regions are described by Romanos et al, 1992, *Yeast* 8:423–488.

Propeptide Sequences

The DNA construct of the invention may also comprise a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the Bacillus subtilis alkaline protease gene (aprE), the Bacillus subtilis neutral protease gene (nprT), the Saccharomyces cerevisiae alpha-factor gene, or the Myceliophthora thermophilum laccase gene (WO 95/33836).

Other Control Sequences

The DNA construct of the present invention may also comprise one or more nucleic acid sequences, which encode one or more factors that are advantageous in the expression of the polypeptide, e.g., an activator (e.g., a trans-acting factor), a chaperone, and a processing protease. Any factor that is functional in the host cell of choice may be used in the present invention. The nucleic acids encoding one or more of these factors are not necessarily in tandem with the structural gene encoding the polypeptide.

An activator is a polypeptide, which activates transcription of a structural gene encoding a polypeptide (Kudla et al., 1990, *EMBO Journal* 9:1355–1364; Jarai and Buxton, 1994, *Current Genetics* 26:2238–244; Verdier, 1990, *Yeast* 6:271–297). The DNA sequence encoding an activator may be obtained from the genes encoding *Bacillus stearothermophilus* NprA (nprA), *Saccharomyces cerevisiae* heme activator protein 1 (hap1), *Saccharomyces cerevisiae* galactose metabolizing protein 4 (gal4), and *Aspergillus nidulans* ammonia regulation protein (areA). For further examples, see Verdier, 1990, supra and MacKenzie et al., 1993, *Journal of General Microbiology* 139:2295–2307.

A chaperone is a protein, which assists another polypeptide in folding properly (Hartl et al., 1994, *TIBS* 19:20–25; Bergeron et al., 1994, *TIBS* 19:124–128; Demolder et al., 1994, *Journal of Biotechnology* 32:179–189; Craig, 1993, *Science* 260:1902–1903; Gething and Sambrook, 1992, *Nature* 355:33–45; Puig and Gilbert, 1994, *Journal of Biological Chemistry* 269:7764–7771; Wang and Tsou, 1993, *The FASEB Journal* 7:1515–11157; Robinson et al, 1994, *Bio/Technology* 1:381-384). The nucleic acid sequence encoding a chaperone may be obtained from the genes encoding *Bacillus subtilis* GroE proteins, *Aspergillus oryzae* protein disulphide isomerase, *Saccharomyces cerevisiae* calnexin, *Saccharomyces cerevisiae* BiP/GRP78, and *Saccharomyces cerevisiae* Hsp70. For further examples, see Gething and Sambrook et al, 1989, Molecular Cloning, A Laboratory Manual, 2d edition, Cold Spring Harbor, N.Y., and Hartl et al, 1994, *TIBS* 19:20–25.

A processing protease is a protease that cleaves a propeptide to generate a mature biochemically active polypeptide (Enderlin and Ogrydziak, 1994, *Yeast* 10:67–79; Fuller et al., 1989, *Proceedings of the National Academy of Sciences USA* 86:1434–1438; Julius et al., 1984, *Cell* 37:1075–1089; Julius et al., 1983, *Cell* 32:839–852). The nucleic acid sequence encoding a processing protease may be obtained from the genes encoding *Aspergillus niger* Kex2, *Saccharomyces cerevisiae* dipeptidylaminopeptidase, *Saccharomyces cerevisiae* Kex2, and *Yarrowia lipolytica* dibasic processing endoprotease (xpr6).

Regulatory Sequences

The DNA construct of the invention may also comprise regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those, which allow for gene amplification. In eukaryotic systems, these include the dihydrofolate reductase gene, which is amplified in the presence of methotrexate, and the metallothionein genes, which are amplified with heavy metals. In these cases, the structural gene encoding a polypeptide would be placed in tandem with the regulatory sequence.

Expression Vectors

The present invention also relates to recombinant expression vectors comprising a DNA sequence or DNA construct of the invention for regulating transcription, and transcriptional and translational stop signals. The various DNA and control sequences described above may be joined together to produce a recombinant expression vector, which may include one or more convenient restriction sites to allow for insertion or substitution of the nucleic acid sequence encoding the polypeptide at such sites. Alternatively, the structural gene encoding a polypeptide may be expressed by inserting the DNA sequence of the invention or a DNA construct into an appropriate vector for expression. In creating the expression vector, the polypeptide coding sequence is located in the vector so that the coding sequence is operably linked with the appropriate control sequences for expression, and possibly secretion.

The recombinant expression vector may be any vector (e.g., a plasmid or virus), which can be conveniently subjected to recombinant DNA procedures and can bring about the expression of the structural gene encoding the polypeptide. The choice of the vector will typically depend on the compatibility of the vector with the eukaryotic host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, a cosmid or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. A frequently used mammalian marker is the dihydrofolate reductase gene. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrg (orotidine-5'-phosphate decarboxylase), sC (sulfate adenyltransferase), trpC (anthranilate synthase), and glufosinate resistance markers, as well as equivalents from other species. Preferred for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the nucleic acid sequence encoding the polypeptide or any other element of the vector for stable integration of the vector into the genome by homologous or none homologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, pACYC184, pUB110, pE194, pTA1060, and pAMβ1. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, *Proceedings of the National Academy of Sciences USA* 75:1433).

The episomal replicating AMA1 plasmid vector disclosed in WO 00/24883 may also be used.

More than one copy of a structural gene encoding a polypeptide may be inserted into the host cell to amplify expression of the structural gene. Stable amplification of the structural gene can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al, 1989, Molecular Cloning, A Laboratory Manual, 2d edition, Cold Spring Harbor, N.Y.).

Eukaryote Host Cells

The invention also relates to eukaryotic host cell comprising a DNA sequence of the invention for regulating transcription or a DNA construct of the invention or an expression vector of the invention. The eukaryotic host cell of the invention comprises a structural gene encoding a polypeptide. The term "host cell" encompasses any progeny of a parent cell, which is not identical to the parent cell due to mutations that occur during replication. The cell is preferably transformed with a vector comprising a DNA sequence for regulating transcription of the invention operably linked to a structural gene followed, in particular by integration of the vector into the host chromosome.

The host cell is a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of *Ascomycota* include, e.g., *Neurospora*, *Eupenicillium* (=*Penicillium*), *Emericella* (=*Aspergillus*), *Eurotium* (=*Aspergillus*), and the true yeasts listed above. Examples of *Basidiomycota* include mushrooms, rusts, and smuts. Representative groups of *Chytridiomycota* include, e.g., *Allomyces, Blastocladiella, Coelomomyces*, and aquatic fungi. Representative groups of Oomycota include, e.g., *Saprolegniomycetous aquatic* fungi (water molds) such as Achlya. Examples of mitosporic fungi include *Aspergillus, Penicillium, Candida,* and *Alternaria*. Representative groups of *Zygomycota* include, e.g., *Rhizopus* and *Mucor*.

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus Schizosaccharomyces), Nadsonioideae, Lipomycoideae, and Saccharomycoideae (e.g., genera Pichia, Kluyveromyces and Saccharomyces). The basidiosporogenous yeasts include the genera *Leucosporidim, Rhodosporidium, Sporidiobolus, Filobasidium,* and *Filobasidiella*. Yeast belonging to the Fungi Imperfecti are divided into two families, Sporobolomycetaceae (e.g., genera Sorobolomyces and Bullera) and Cryptococcaceae (e.g., genus Candida). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast*, Bacil, M., Horecker, B. J., and Stopani, A. O. M., editors, 2nd edition, 1987; *The Yeasts*, Rose, A. H., and Harrison, J. S., editors, 2nd edition, 1987; *and The Molecular Biology of the Yeast Saccharomyces*, Strathern et al., editors, 1981).

In a more preferred embodiment, the yeast host cell is a cell of a species of *Candida, Kluyveromyces, Saccharomy-* ces, *Schizosaccharomyces, Pichia*, or *Yarrowia*. In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In a preferred embodiment, the fungal host cell is a filamentous fungal cell. "Filamentous fungi" include all filamentous forms of the subdivision Eumycota and Oomycota (as defined by Hawksworth et al., In, *Ainsworth and Bisby's Dictionary of The Fungi*, 8th edition, 1995, CAB International, University Press, Cambridge, UK. The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium*, and *Trichoderma* or a teleomorph or synonym thereof. In an even more preferred embodiment, the filamentous fungal host cell is an *Aspergillus* cell. In another even more preferred embodiment, the filamentous fungal host cell is an *Acremonium* cell. In another even more preferred embodiment, the filamentous fungal host cell is a *Fusarium* cell. In another even more preferred embodiment, the filamentous fungal host cell is a *Humicola* cell. In another even more preferred embodiment, the filamentous fungal host cell is a *Mucor* cell. In another even more preferred embodiment, the filamentous fungal host cell is a *Myceliophthora* cell. In another even more preferred embodiment, the filamentous fungal host cell is a *Neurospora* cell. In another even more preferred embodiment, the filamentous fungal host cell is a *Penicillium* cell. In another even more preferred embodiment, the filamentous fungal host cell is a *Thielavia* cell. In another even more preferred embodiment, the filamentous fungal host cell is a *Tolypocladium* cell. In another even more preferred embodiment, the filamentous fungal host cell is a *Trichoderma* cell. In a most preferred embodiment, the filamentous fungal host cell is an *Aspergillus awamori, Aspergillus foetidus, Aspergillus japonicus, Aspergillus niger* or *Aspergillus oryzae* cell. In another most preferred embodiment, the filamentous fungal host cell is a Fusarium cell of the section Discolor (also known as the section Fusarium). For example, the filamentous fungal parent cell may be a *Fusarium bactridioides, Fusarium cerealis, Fusarium crookwellense, Fusarium culmorum, Fusarium graminearum, Fusarium graminum, Fusarium heterosporum, Fusarium negundi, Fusarium reticulatum, Fusarium roseum, Fusarium sambucinum, Fusarium sarcochroum, Fusarium sulphureum*, or *Fusarium trichothecioides* cell. In another prefered embodiment, the filamentous fungal parent cell is a Fusarium strain of the section Elegans, e.g., *Fusarium oxysporum*. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

The host cell of the invention may be a protease transcription activator less strain, in particular a prtT gene deleted strain. In particular the host cell may be an *Aspergillus*, such as *A. niger* or *A. oryzae* strain as described in WO 00/20596.

Transformation of Eukaryote Host Cells

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81:1470–1474. A suitable method of transforming *Fusarium* species is described by Malardier et al., 1989, *Gene* 78:147–156 or in copending U.S. Ser. No. 08/269,449. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182–187, Academic Press, Inc., New York; Ito et al., 1983, *Journal of Bacteriology* 153:163; and Hinnen et al., 1978, *Proceedings of the National Academy of Sciences USA* 75:1920. Mammalian cells may be transformed by direct uptake using the calcium phosphate precipitation method of Graham and Van der Eb (1978, *Virology* 52:546).

Cultivation of Host Cell

The methods used for cultivation of microbial or plant host cells are known in the art.

Methods of the Invention

In an aspect the invention relates to a method of producing a polypeptide, comprising:

(a) cultivating a host cell of the invention, wherein the host cell harbours a structural gene under control of a DNA sequence of the invention, in a nutrient medium suitable for production of the polypeptide; and (b) recovering the polypeptide from the nutrient medium.

The host cell may be any of the above mentioned. The DNA sequence of the invention may be located upstream to a structural gene encoding a polypeptide, which may be native or foreign to the host cell.

The invention also relates to a method of increasing the transcription and/or expression levels of a eukaryotic host cell comprising introducing one or more RNA polymerase binding sites upstream to a parent RNA polymerase binding site or promoter.

The term "parent" RNA polymerase binding site or promoter means the site or promoter present in the host cell before modification. The method can be used to provide host cell for both homologous and heterologous production. In a homologous host the promoter may be replaced with a DNA sequence of the invention.

In an embodiment the DNA sequence of the invention for regulating transcription is introduced upstream to the structural gene or the parent RNA polymerase binding site or promoter is replaced with the DNA sequence of the invention. In an embodiment the introduced RNA polymerase binding sites consists of one or more repetitive DNA sequences which is capable of binding RNA polymerase.

In an embodiment RNA polymerase binding sites are tandem sites.

MATERIALS & METHODS

Chemicals used as buffers and substrates were commercial products of at least reagent grade.

Media and Solutions

MY25 medium at pH 6.5 was composed per liter (L) of 25 g of maltose, 2.0 g of $MgSO_4.7H_2O$, 10 g of $KH_2PO_4$, 2.0 g of citric acid, 10 g of yeast extract, 2.0 g of $K_2SO_4$, 2.0 g of urea, 1.0 mL of $CaCl_2.2H_2O$ (100 g/l stock solution), and 0.5 mL of trace metals solution. MY25 microtiter medium was diluted 1:100 with 490 mL glass distilled water and 500 mL 2×MY Salts. Cultures were grown at 30° C.

2×MY Salts pH 6.5 solutions was composed per liter of 4 g of $MgSO_4.7H_2O$, 4 g of $K_2SO_4$, 20 g of $KH_2PO_4$, 4 g of citric acid, 1 mL of trace metals solution, and 2 mL of $CaCl_2.2H_2O$ (100 g/l stock solution).

Minimal medium transformation plates were composed per liter of 6 g of $NaNO_3$, 0.52 g of KCl, 1.52 g of $KH_2PO_4$, 1 mL of trace metals solution, 10 g of glucose, 500 mg of $MgSO_4.7H_2O$, 342.3 g of sucrose, and 20 g of Noble agar (pH 6.5). Minimal medium transfer plates (pH 6.5) were composed per liter of 6 g of $NaNO_3$, 0.52 g of KCl, 1.52 g of $KH_2PO_4$, 1 mL of trace elements, 1 g of glucose, 500 mg of $MgSO_4.7H_2O$, and 20 g Noble agar.

Minimal Medium was composed per liter of 6 g of $NaNO_3$, 0.52 g of KCl, 1.52 g of $KH_2PO_4$, 1 mL trace metals, 10 g of glucose, 500 mg of $MgSO_4.7H_2O$, 342.3 g of sucrose, and 20 g of Noble agar at pH 6.5. Transfer plates were the same as above, but omitting the sucrose.

The trace metals solution (1000×) was composed per liter of 22 g of $ZnSO_4.7H_2O$, 11 g of $H_3BO_3$, 5 g of $MnCl_2.4H_2O$, 5 g of $FeSO_4.7H_2O$, 1.6 g of $CoCl_2.5H_2O$, 1.6 g of $(NH_4)_6Mo_7O_{24}$, and 50 g of $Na_4EDTA$.

Chlorate plate was composed of Minimal Medium supplemented 470 mM chlorate and 10 mM glutamate as sole nitrogen source.

YPM medium was composed per liter of 5 g yeast extract, 10 g Bacto peptone, and 2 g Maltose.

AMG trace-element solution is composed of 2.5 g of $CuSO_4.5H_2O$, 6.8g of $ZnCl_2$, 0.24 g of $NiCl_2.6H_2O$, 13.9 g of $FeSO_4.7H_2O$, 13.6 g of $MnSO_4.5H_2O$, and 3.0 g of Citric acid monohydrate (Wako No. 035-03495), water to 1 liter.

GO-50 is composed of 50 g of glucose, 2 g of $KH_2PO_4$, 2 g of $MgSO_4.7H_2O$, 3 g of $K_2SO_4$, 2 g of citric acid monohydrate (Wako No. 035-03495), 50 g of oxalic acid.$2H_2O$, 0.5 ml of AMG trace element solution and 50 g of oxalic acid.$2H_2O$ (pH 4.5), water to 1 liter. Before use 3 ml of 10% Urea is added.

Cove-N plates are composed of 342.3 g of sucrose, 3 g of $NaNO_3$, 20 ml of Cove salt solution, and 30 g of noble agar, water to 1 liter.

Cove salt solution is composed of 26 g of KCl, 26 g of $MgSO_4.7H_2O$, 76 g of $KH_2PO_4$ and 50 ml Cove trace-element J solution, water to 1 liter.

Cove top agarose is composed of 342.3 g of Sucrose, 20 ml of Cove salt solution, 3 g of $NaNO_3$ and 10 g of low melt agarose, water to 1 liter.

Cove trace-element J solution is composed of 0.04 g $NaB_4O_7.10H_2O$, 0.4 g of $CuSO_4.5H_2O$, 1.2 g of $FeSO_4.7H_2O$, 1.0 g of $MnSO_4.H_2O$, 0.8 g of $Na_2MoO_2.2H_2O$, and 10.0 g of $ZnSO_4.7H_2O$, water to 1 liter.

Cove-N2 plates are composed of 30 g of sucrose, 20 ml of Cove salt solution, 3 g of $NaNO_3$ and 30 g if noble to 1 liter.

MLC is composed of 50 g of soybean powder, 40 g of glucose, and 4 g citric acid monohydrate (Wako No. 035-03495), water to 1 liter (pH 5.0).

STC buffer is composed of 0.8 M of sorbitol, 25 mM of Tris (pH 8), and 25 mM of $CaCl_2$, water to 1 liter.

STPC buffer is composed of 40% PEG4000 in STC buffer.

YPG medium is composed of 4 g of yeast extract, 1 g of $KH_2PO_4$, 0.5 g of $MgSO_4.7H_2O$ and 15 g of Glucose, water to 1 liter (pH 6.0).

Strains

JaL228: The construction of this strain is described in patent WO 98/12300.

JaL250: The construction of this strain is described in Example 7.

JaL294: The construction of this strain is described in Example 8.

MBin119: *Aspergillus niger* expression host MBin119 is a strain genetically modified to disrupt expression of glucoamylase, acid-stable alpha-amylase, neutral amylase I and II, pyrG and alpha-1,6 transglucosidase activities.

Plasmids pNA2: The construction is described in patent WO 89/01969.

p960 The construction is described in patent EP 0305,206 A1.

pJeRS4: The construction is described in U.S. Pat. No. 5,861,280 pIC19H: The construction is described in Marsh et al, 1984, Gene 32:481–485.

pUC19: The construction is described in Vieira et al, 1982, Gene 19:259–268 pSTA14: are described in Unkles et al., 1989, *Molecular General Genetics* 218: 99–104 pJaL211: The construction is described in example 1.

pJaL240: The construction is described in example 2.

pToC108: The construction is described in example 3 pJaL410: The construction is described in example 3.

pJaL420: The construction is described in example 3.

pJaL423: The construction is described in example 3.

pJaL475: The construction is described in example 3.

pJaL479: The construction is described in example 3.

pJaL485: The construction is described in example 3.

pJaL535: The construction is described in example 4.

pJaL676: The construction is described in example 5.

pToC432: The construction is described in example 6.

pJaL419: The construction is described in example 8.

pJaL448: The construction is described in example 8.

pJaL700: The construction is described in example 9.

pJaL701: The construction is described in example 10.

pJaL724: The construction is described in example 11.

pJaL729: The construction is described in example 12.

pJaL719: The construction is described in Example 16.

pJaL721: The construction is described in Example 17.

The plasmid pCaHj483 comprises *A. niger* Neutral-amylase 2 promoter (NA2), the *Aspergillus nidulans* TPI leader sequences, the *Aspergillus niger* glucoamylase terminator and the *A. nidulans* amdS gene.

Transformation of *Aspergillus niger*

Transformation of *Aspergillus niger* can be achieved with general protoplasts methods. The preferred procedure for the invention is described below.

The host strain is propagated in 100 ml of non-selective YPG medium at 32□ C. for 16 hrs on a rotary shaker at 120 rpm. Cells are collected by filtering, washed with 0.6 M KCl and resuspended in 20 ml of 0.6 M KCl containing a commercial beta-glucanase product (GLUCANEX™, Novozymes A/S) at 600 microL/ml. The suspension is incubated at 32° C. at 80 rpm until protoplasts are formed, then washed twice with STC buffer. The protoplasts are counted with a hematometer and resuspended and adjusted in an 8:2:0.1 solution of STC:STPC:DMSO to a final concentration of $2.5 \times 10^7$ protoplasts/ml. About 3 microgram of DNA is added to 100 microL of protoplast suspension, mixed gently and incubated on ice for 20 min. One ml of SPTC is added and the protoplast suspension is incubated for 30 min at 37° C. After the addition of 10 ml of 50° C. Cove top agarose, the reaction is poured onto Cove-N agar plates and the plates are incubated at 32° C. for 5 days. As untransformed cells cannot grow on Cove-N medium, transformants are easily selected.

EXAMPLES

Example 1

Construction of pJaL211

Plasmid pJaL211 was constructed to contain the *A. niger* neutral amylase 2 (NA2) promoter.

The 923 bp HindIII-BamHI fragment from pNA2 was ligated to the 4278 bp HindIII-BamHI fragment from p960, resulting in pJaL211.

Example 2

Construction of pJaL240

Plasmid pJaL240 was constructed to contain a 611 bp fragment of the *A. niger* neutral amylase 2 (NA2) promoter.

The 611 bp EcoRI-BamHI fragment from pJaL211 was ligated to the 2690 bp EcoRI-BamHI fragment from pIC19H, resulting in pJaL240.

Example 3

Construction of pJaL485

Plasmid pJaL485 was constructed to contain the truncated niaD gene and an expression cassette where the *Humicola lanuginosa* lipase gene was sandwiched between the NA2 promoter and the *Aspergillus niger* AMG terminator.

Plasmid pSTA14 encoding the *Aspergillus oryzae* niaD gene (Unkles et al,. 1989, *Molecular General Genetics* 218: 99–104) was digested with HindIII and the 5136 bp fragment was purified and cloned into pUC19 digested with HindIII to yield plasmid pToC108. Plasmid pToC108 was digested with BglII-SalI and the 3700 bp fragment was purified and cloned into pUC19 digested with BglII-SalI to yield plasmid pJaL410. This plasmid is encoding a truncated niaD gene wherein the 85 N-terminal amino acids have been removed.

Plasmid pJaL410 was digested with SacI-PstI and treated with Klenow and dNTP's and the 6018 bp fragment was purified and religated to yield plasmid pJaL420. The BamHI site in pJaL420 was removed by making a silent mutation by using the Chameleon Double-Stranded Site-Directed Mutagenesis Kit (Stratagene Cloning Systems, La Jolla, Calif.) according to the manufacturer's instructions giving plasmid pJaL423. The BamHI site was destroyed by changing the T in the BamHI site to a C using the following primer:

5'-GGAACGATGGACCCGGAAGGTTTAAAAGC-3' (SEQ ID NO: 2)

Sequencing around the destroyed BamHI site revealed that further downstream there was some unexpected changes, which resulted in a frame shift in the niaD gene and the creation of a SmaI site. To repair this frame shift the 291 bp AccI-DraI fragment in pJaL423 was exchanged with the corresponding fragment from pJaL420 to give pJaL475.

The 3381 bp HindIII fragment from pJaL475 encoding the truncated niaD gene was cloned into the HindIII site of plasmid pJaL211, resulting in plasmid pJaL479. The HindIII site at position 2 was destroyed by partial digestion with HindIII followed by treatment with Klenow and dNTP's. The 8586 bp fragment was purified and religated to yield plasmid pJaL485.

Example 4

Construction of pJaL535

Plasmid pJaL535 was constructed to contain the truncated niaD gene and an expression cassette where the *Humicola lanuginosa* lipase gene was sandwiched between the NA2 promoter (shown in position 7–510 of SEQ ID NO: 1) and the *Aspergillus niger* AMG terminator.

The 644 bp HindIII-BamHI fragment from pJaL240 was ligated to the 7663 bp HindIII-BamHI fragment from pJaL485, resulting in pJaL535.

Example 5

Construction of pJaL676

Plasmid pJaL676 is a derivative of pJaL535 where the NA2 promoter shown in position 7–510 of SEQ ID NO: 1 has been modified in several runs of site directed mutagenesis by a simple PCR approach.

Nucleotides 135–145 were altered from SEQ ID NO: 3 to SEQ ID NO: 4 using the mutagenic primer in SEQ ID NO: 5.

Nucleotides 407–422 were altered from SEQ ID NO: 6 to SEQ ID NO: 7 using the mutagenic primer in SEQ ID NO: 8.

Nucleotides 424–437 were altered from SEQ ID NO: 9 to SEQ ID NO: 10 using the mutagenic primer in SEQ ID NO: 11.

Nucleotides 529–617 were altered from SEQ ID NO: 12 to SEQ ID NO: 13 using the mutagenic primer in SEQ ID NO: 14.

The resulting plasmid was termed pJaL676.

Example 6

Construction of pToC432

Plasmid pToC432 is a derivative of pJaL535 where the NA2 promoter shown in position 7–510 of SEQ ID NO: 1 has been modified in several runs of site directed mutagenises by a simple PCR approach.

Nucleotides 135–145 were altered from SEQ ID NO: 3 to SEQ ID NO: 4 using the mutagenic primer in SEQ ID NO: 5.

Nucleotides 407–422 were altered from SEQ ID NO: 6 to SEQ ID NO: 7 using the mutagenic primer in SEQ ID NO: 8.

Nucleotides 529–617 were altered from SEQ ID NO: 12 to SEQ ID NO: 13 using the mutagenic primer in SEQ ID NO: 14.

The resulting plasmid was termed pToC432.

Example 7

Isolation of a PyrG minus *Asperqillus oryzae* JaL250

The *A. oryzae* strain JaL228, described in WO 98/12300, was screened for resistance to 5-flouro-orotic acid to identify spontaneous pyrG mutants. One strain, named JaL250, was identified as being pyrG minus. The mutant is uridine dependent, therefore it can be transformed with the wild type pyrG gene and transformants selected by the ability to grow in the absence of uridine.

Example 8

Construction of *Aspergillus oryzae* JaL294

For construction of a defined *Aspergillus oryzae* niaD mutant a replacement plasmid pJaL448 was constructed where the C-terminal part of the niaD gene was replaced by the *Aspergillus oryzae* pyrG gene.

Plasmid pJaL410 (construction described in Example 3) was digested with KpnI and the 4307 bp fragment was purified and religated to yield plasmid pJaL419. Plasmid pJeRS4 encoding the *Aspergillus oryzae* pyrG gene was digested with KpnI and the 1515 bp fragment was purified and ligated with pJaL419 digested with KpnI to yield pJaL448.

Plasmid pJaL448 is a double cross-over plasmid where the *Aspergillus oryzae* pyrG gene (1515 bp KpnI fragment from pJeRS4) is flanked by a 782 bp BglII-KpnI fragment encoding amino acid 85 to 276 of the niaD protein and by a 841 bp KpnI-HindIII fragment containing the niaD terminator.

Protoplasts preparation of *Aspergillus oryzae* JaL250: The *Aspergillus oryzae* JaL250 was grown in 100 mL of YEG medium at 34° C. for 16–18 hours with agitation at 160 rpm. The mycelia were recovered by filtration through a 0.2 micro m filter until approximately 10 mL remained on the filter, washed with approximately 20 ml of 1 M MgSO$_4$.7H$_2$O (0.2 micro m filtered), and then collected with a sterile loop and placed in a 125 mL Ehrlenmeyer flask. The mycelia were then resuspended with 75 mg of NOVOZYM 234™ (from Novozymes A/S, Bagsvaerd, Denmark) in 15 mL of 1 M MgSO$_4$.7H$_2$O. The suspension was incubated at 37° C. with gentle agitation at 50 rpm for approximately one hour to generate protoplasts.

The contents of the 125 mL Ehrlenmeyer flask was then filtered through sterile Miracloth into a 30 mL Corex centrifuge tube, overlaid with 6 mL of 0.6 M sorbitol-100 mM Tris pH 7.0, and centrifuged at 3500×g for 15 minutes in a swinging bucket rotor to recover the protoplasts. The protoplasts were recovered from the buffer interface with a Pasteur pipet. The protoplasts were then washed with two volumes of STC (1.2 M sorbitol-10 mM Tris-10 mM CaCl$_2$.2H$_2$O pH 7.5) and centrifuged at 3500×g for 5 minutes. The protoplasts were washed two times in 10 mL of STC and centrifuged as before. The protoplasts were resuspended in STC to a final concentration of 1.7×10$^7$ protoplasts per mL. pJaL448 was linearized with XhoI and transformed into protoplasts of *Aspergillus oryzae* JaL250.

Transformation of *Aspergillus oryzae* JaL250 for chlorate resistance selection was conducted with protoplasts at a concentration of 1.7×10$^7$ protoplasts per mL. Ten micro g of linearized pJaL448 were added to 100 microL of protoplasts. A volume of 250 microL of PEG solution (60% PEG 4000–10 mM CaCl$_2$) was then added and the mixture was placed at 37° C. for 30 minutes. Four mL STC was then added and the mixture was plated onto Minimal media plates selecting for chlorate resistance. The plates were incubated 5–7 days at 37° C. Chlorate resistance transformants (9 out 45) were isolated and further purified on chlorate-containing minimal medium with glutamate as the sole source of nitrogen. The ability of these 9 mutants to grow on nitrate and nitrite as sole nitrogen source was assessed. Three had a phenotype indicative of nitrate reductase structural mutants (niaD), i.e., they failed to grow with nitrate but grew on nitrite as sole nitrogen source.

Southern analysis of BamHI-, KpnI-, and HindIII-digested genomic DNA from the three mutant strains, probed with either the 2 kb KpnI fragment or with the 3.7 kb HindIII fragment from pJaL410, demonstrated that only one of the transformants, designated *Aspergillus oryzae* JaL294, has the expected gene replacement at the niaD locus.

Example 9

Construction of pJaL700

Plasmid pJaL700 is a derivate of pToC432 where part of the NA2 promoter from position 7 to 510 has been duplicated. By PCR with primers SEQ ID NO: 15 and SEQ ID NO: 16 a 534 bp DNA fragment was amplified from pToC432, purified, and digested with the restriction endonucleases EcoRI and HindIII, resulting in a 516 bp DNA fragment. The 516 bp DNA fragment was ligated together with the 8283 bp HindIII-EcoRI DNA fragment from pJaL676, resulting in plasmid pJaL700 (FIG. 1).

Example 10

Construction of pJaL701

Figure 2:
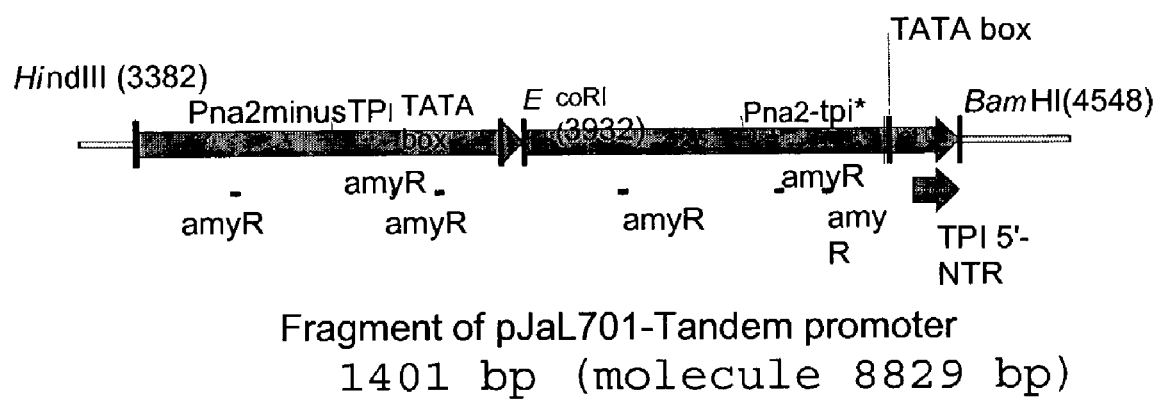
FIG. 2 shows a restriction map of pJaL701.

Plasmid pJaL701 is a derivate of pToC432 where part of the NA2 promoter from position 7 to 510 has been duplicated. By PCR with primers SEQ ID NO: 15 and SEQ ID NO: 17 a 574 bp DNA fragment was amplified from pToC432, purified, and digested with the restriction endonucleases EcoRI and HindIII, resulting in a 556 bp DNA fragment. The 556 bp DNA fragment was ligated together with the 8283 bp HindIII-EcoRI DNA fragment from pJaL676, resulting in plasmid pJaL701(FIG. 2).

Example 11

Construction of pJaL724

Plasmid pJaL724 is a derivate of pJaL676 where part of the NA2 promoter from position 7 to 510 has been duplicated. By PCR with primers SEQ ID NO: 15 and SEQ ID NO: 16 a 538 bp DNA fragment was amplified from pJaL676, purified, and digested with the restriction endonucleases EcoRI and HindIII, resulting in a 514 bp DNA fragment. The 514 bp DNA fragment was ligated together with the 8283 bp HindIII-EcoRI DNA fragment from pJaL676, resulting in plasmid pJaL724.

Example 12

Construction of pJaL729

Plasmid pJaL729 is a derivate of pJaL676 where part of the NA2 promoter from position 7 to 510 has been triplicated. By PCR with primers SEQ ID NO: 15 and SEQ ID NO: 16 a 538 bp DNA fragment was amplified from pJaL676, purified, digested with the restriction endonucleases EcoRI, and was blunt ended by treatment with Klenow polymerase and dNTP's, resulting in a 520 bp DNA fragment. The 520 bp DNA fragment was ligated together with the 8797 bp HindIII DNA fragment from pJaL724, resulting in plasmid pJaL729.

Example 13

Transformation of *Aspergillus oryzae* JaL294

*Aspergillus oryzae* JaL294 was grown in 100 mL of YEG medium at 34° C. for 16–18 hours with agitation at 160 rpm. The mycelia were recovered by filtration through a 0.2 micro m filter until approximately 10 mL remained on the filter, washed with approximately 20 mL of 1 M $MgSO_4.7H_2O$ (0.2 micro m filtered), and then collected with a sterile loop and placed in a 125 mL Ehrlenmeyer flask. The mycelia were then resuspended with 75 mg of NOVOZYM 234™ (Novozymes A/S, Bagsvaerd, Denmark) in 15 mL of 1 M $MgSO_4.7H_2O$. The suspension was incubated at 37° C. with gentle agitation at 50 rpm for approximately one hour to generate protoplasts.

The contents of the 125 mL Ehrlenmeyer flask was then filtered through sterile Miracloth into a 30 mL Corex centrifuge tube, overlaid with 6 mL of 0.6 M sorbitol-100 mM Tris pH 7.0, and centrifuged at 3500×g for 15 minutes in a swinging bucket rotor to recover the protoplasts. The protoplasts were recovered from the buffer interface with a Pasteur pipet. The protoplasts were then washed with two volumes of STC (1.2 M sorbitol-10 mM Tris-10 mM $CaCl_2.2H_2O$ pH 7.5) and centrifuged at 3500×g for 5 minutes. The protoplasts were washed two times in 10 mL of STC and centrifuged as before. The protoplasts were resuspended in STC to a final concentration of $1.7 \times 10^7$ protoplasts per mL.

Transformation of *Aspergillus oryzae* JaL294 for niaD selection was conducted with protoplasts at a concentration of $1.7 \times 10^7$ protoplasts per mL. Five micro g of DNA (pToC432, pJaL676, pJaL700, pJaL701, pJaL724, or pJaL729) were added to 100 microL of protoplasts. A volume of 250 microL of PEG solution (60% PEG 4000–10 mM $CaCl_2$) was then added and the mixture was placed at 37° C. for 30 minutes. Four mL STC was then added and the mixture was plated onto Minimal media plates selecting for niaD. The plates were incubated 5–7 days at 37° C. The transformants were purified by streaking spores and picking isolated colonies from Minimal media plates incubated at 37° C.

Example 14

Characterization of Integration Events in *Asperqillus oryzae* JaL294 transformants Genomic DNA was isolated from all of the *Aspergillus oryzae* JaL294 transformants according to the following procedure. Each transformant was grown in 10 mL of YPM medium for 24 hours at 30° C. in a 25 mL test tube (NUNC container). Mycelia were then collected from each culture by filtration through Whatman filter paper No. 1 (Whatman, Springfield Mill, England) and transferred to a 1.7 mL centrifuge tube. The mycelia preparations were frozen in liquid nitrogen and dried in a Speed-Vac (Savant Instruments, Inc., Farmingdale, N.Y.) for 1.5 hours. The frozen mycelia preparations were ground to a fine powder with a sterile toothpick. A Qiagen DNeasy Kit (QIAGEN, Inc., Valencia, Calif.) was used to extract the genomic DNA from the frozen mycelia following the manufacturer's instructions.

The genomic DNA was digested with PstI and then Southern hybridization was used to determine whether there was a single copy of the plasmid integrated into the transformants according to the procedure described by Sambrook et al., 1989, supra. Additionally, genomic DNA was extracted from untransformed *Aspergillus oryzae* JaL294. Southern blots of the digests were probed with a 1.8 kb niaD fragment obtained from pToC108. The fragment was labeled with dioxygenin using a Boehringer Mannheim PCR DIG Probe Synthesis Kit (Boehringer Mannheim, Indianapolis, Ind.) according to the manufacturer's instructions. The blot was prehybridized for 2 hours and hybridized overnight at 50° C. in DIG Easy Hyb. The blot was washed and processed as recommended by the manufacturer.

The Southern blot demonstrated that pJaL485 contained a 8.5 kb band and untransformed *Aspergillus oryzae* JaL294 contained a 3.8 kb band when probed with the niaD fragment. Transformants in which a single copy of the plasmid was integrated should contain an 11.7 kb and 3.8 kb bands. Transformants in which multiple copies of the plasmid were integrated should contain the same 11.7 kb and 3.8 kb bands as well as a third band of 8.5 kb. Those transformants, which had integrated a single copy of the plasmid DNA, were then grown in shake flask and subsequently assayed for lipase expression.

Example 15

Analysis of Transformants in Shake Flask

The *Aspergillus oryzae* JaL294 transformants obtained in Example 13 were assayed for lipase expression. For microtiter assays, MY25 medium was diluted 100 fold with 49% glass distilled water and 50% 2×MY Salts pH 6.5 solution. A volume of 1.25 mL of 1/100 strength MY25 medium was added to the wells of a 24 well cell culture plate. The wells were inoculated with 10 microL of spores from each transformant, and the plates were incubated at 34° C. with agitation at 100 rpm. Each transformant was inoculated into three wells. Untransformed *Aspergillus oryzae* JaL294 was used to inoculate three wells.

Samples of 100 microL were removed on days 2 and 4 from each well of the 24 well cell culture plates. Each sample was diluted with 200 microL of 100 mM alpha olefin sulfonate (AOS) detergent in 4 mM $CaCl_2$-100 mM MOPS pH 7.5 (MC buffer) and 20 microL aliquots were dispensed to wells in 96-well plates followed by 200 microL of diluted substrate. The lipase assay substrate was prepared by diluting 1:50 a p-nitrophenylbutyrate stock substrate (21 microL of p-nitrophenylbutyrate/mL DMSO) into MC buffer immediately before use. Standard lipase (LIPOLASE™, Novozymes A/S, Bagsvaerd, Denmark) was prepared to contain 40 LU/mL of MC buffer containing 0.02% AOS detergent. The standard was stored at 4° C. until use. Standard lipase was diluted 1/40 in MC buffer just before use. Using a plate reader, the absorbance at 405 nm was recorded as the difference of two readings taken at approximately 1-minute intervals. Lipase units/mL (LU/mL) were calculated relative to the lipase standard. The results of the lipase assays for day 4 are shown in Table I and Table 2 relative to lipase activity obtained with pToC432 and pJaL676, respectively.

TABLE 1

Lipase expression by *Aspergillus oryzae* JaL294 transformants with pToC432, pJaL700, and pJaL701

| Plasmid | # Transformants screened | Mean lipase activity |
|---|---|---|
| pToC432 | 2 | 1 |
| pJaL700 | 2 | 1.77 |
| pJaL701 | 2 | 1.52 |

TABLE 2

Lipase expression by *Aspergillus oryzae* JaL294 transformants with pJaL676, pJaL724, and pJaL729

| Plasmid | # Transformants screened | Mean lipase activity |
|---|---|---|
| pJaL676 | 2 | 1.00 |
| pJaL724 | 2 | 1.23 |
| pJaL729 | 2 | 1.63 |

As shown in Table 1 where two different parts of the NA2 promoter sequences are duplicated there was significant increase in expression of lipase for both constructions as compared to the wild type plasmid (pJaL485).

As shown in table 2 where a part of the NA2 promoter in pJaL676 has been duplicated or triplicated there was significant increase in expression of lipase for both constructions as compared to the wild type plasmid (pJaL676)—with the highest expression from the promoter that has been triplicated.

Example 16

Construction of pJaL719

The *Aspergillus* expression plasmid pCaHj527 (WO 0070064) consists of an expression cassette based on the *Aspergillus niger* neutral amylase II promoter fused to the *Aspergillus nidulans* triose phosphate isomerase non translated leader sequence (NA2/tpi) and the *Aspergillus niger* amyloglycosidase terminater (Tamg). Also present on the plasmid is the *Aspergillus* selective marker amdS from *Aspergillus nidulans* enabling growth on acetamide as sole nitrogen source and the URA3 marker from *Sacchammyces cerevisiae* enabling growth of the pyrf defective *Escherichia coil* strain DB6507 (ATCC 35673). Transformation into *E. coli* DB6507 using the *S. cerevisiae* URA 3 gene as selective marker was done in the following way:

The NA2/tpi promoter present on pCaHj527 was subjected to site directed mutagenesis by a simple PCR approach.

Nucleotides 134–144 were altered from SEQ ID NO: 3 to SEQ ID NO: 4 using the mutagenic primer 141223 (SEQ ID NO: 5).

Nucleotides 423–436 were altered from SEQ ID NO: 6 to SEQ ID NO: 7 using the mutagenic primer 141222 (SEQ ID NO: 8).

The resulting plasmid was termed pMT2188.

The 6352 bp EcoRI-BamHI fragment from pMT2188 and the 617 bp EcoRI-BamHI fragment from pJaL676 where ligated together resulting in plasmid pJaL719.

Example 17

Construction of pJaL721

Plasmid pJaL721 is a derivate of pJaL719 where part of the NA2 promoter from position 7 to 510 has been duplicated. By PCR with primers SEQ ID NO: 15 and SEQ ID NO: 16 a 538 bp DNA fragment was amplified from pJaL676, purified, and digested with the restriction endonucleases EcoRI, resulting in a 520 bp DNA fragment. The 520 bp DNA fragment was ligated together with the 6355 bp EcoRI DNA fragment from pJaL719, resulting in plasmid pJaL721.

Example 18

Construction for plasmid pPME/267

A strain of *Aspergillus niger* was used as a genomic clone of PME (pectin methyl esterase) DNA supplier.

PCR reactions on *Aspergillus niger* genomic DNA was done with two following primers which include a BgI II and a Xho I restriction enzyme site, respectively.

```
BgIIIaccPME->
atagatctaccatggttaagtcaattcttgca    (SEQ ID NO:18)
  BgI II

XhoPME<-
atctcgagaccgcttacaactttcacacaagt    (SEQ ID NO:19)
  Xho I
```

The reaction mixture comprised 2.6 ng/micro L of genomic DNA, 0.25 mM of dNTP, 100 pmol of each primer and 3.5 units of EXPAND™ polymerase in 100 microL of the provided buffer with $MgCl_2$. PCR was performed under the following conditions: The reaction was submitted to 94° C. for 2 minutes followed by 30 cycles of 94° C. for 15 sec, 60° C. for 30 sec and extension at 72° C. for 1 minute. From cycle 11 to 30 the duration of the 72° C. extension step was prolonged with 20 sec per cycle. A final extension step at 70° C. for 7 minutes followed by a 4° C. hold step completed the program.

The amplified 1.3 kb PME gene was gel purified and ligated into pT7blue and the resulting plasmid was termed pt-vPME. pt-vPME was sequenced and confirmed to be identical to EMBL:A34997.

To synthesize NA2 leader sequence, PCR amplification was performed using the primers rika1 (SEQ ID NO: 20) and rika2 (SEQ ID NO: 21). rika2 includes a BamH I site.

```
rika1:
aaatactggcaagggatgccatgcttggaggatagcaaccgacaacatcacatcaagctctcccttct  (SEQ ID NO:20)

rika2:
atggatcccttctgtggggtttattgttcagagaagggagagcttgatgtgatgttgtcggttgctatc  (SEQ ID NO:21)
BamHI
```

BamHI

The reaction mixture comprised 0.25 mM of dNTP, 100 pmol of each primer and 3.5 units of EXPAND™ polymerase in 100 microL of provided buffer with $MgCl_2$. PCR was performed under the following conditions. The reaction was submitted to 94° C. for 2 minutes followed by 30 cycles of 94° C. for 15 sec, 60° C. for 30 sec and extension at 72° C. for 45 sec. A final extension step at 70° C. for 7 minutes followed by a 4° C. hold step completed the program. The amplified DNA fragment encoding NA2 leader was gel purified and named rika3.

To replace the TPI leader sequence of pJaL719 with NA2 leader, PCR amplification was performed using the primers rika3 which was synthesized in the previous PCR reaction and rika4 (SEQ ID NO: 22). The two primers contain the restriction site BamH I and EcoR I, respectively.

```
                                            (SEQ ID NO:22)
rika4: atgaattcatggtgttttgatcattttaaattttat
       EcoR I
```

The reaction mixture comprised 10 ng of pJaL719 as template, 0.25mM of dNTP, 100 pmol of each primer and 3.5 units of EXPAND™ polymerase in 100 microL of provided buffer with $MgCl_2$. The reaction was submitted to 94° C. for 2 minutes followed by 30 cycles of 94° C. for 15 sec, 60° C. for 30 sec and extension at 72° C. for 45 sec. From cycle 11 to 30 the duration of the 72° C. extension step was prolonged with 20 sec per cycle. A final extension step at 72° C. for 7 minutes followed by a 4° C. hold step completed the program.

The 0.6kb amplified DNA fragment containing NA2 promoter region with three extra amyR binding sites was cut by EcoRI and BamHI and ligated into pCaHj483 cut by EcoRI and BamH I and transformed to DH5-alpha. The transformants were then screened by restriction digesting of extracted plasmid DNA with EcoRI and BamHI followed by plasmid extraction and sequencing as described above for control of correct sequence. The plasmid was named pHUda260 having A. niger NA2 promoter with NA2 leader sequences and three extra amyR binding sites, A. niger AMG terminator and A. niduluns amdS gene.

The plasmid was linearized by SphI digestion. The 6.8 kb linearized pHUda260 was filled-in by T4 DNA polymerase and digested with XbaI. The 4.0 kb DNA fragment was gel-purified and ligated with 2.3 kb DNA fragment having Kozac sequences modified A. niger pyrG gene generated from pHUda285 by PmeI and SpeI digestion. The ligated mixture was transformed into JM109. The resulted plasmid was pHUda263.

The tandem NA2 promoter region with three extra amyR binding sites without leader sequences was amplified from pJaL721 by PCR with the primers NA2F and NA2R which included a MfeI and a EcoRI restriction enzyme site, respectively.

```
NA2F;
5'-tttcaattgaagcttatggtgttttgat-3'    (SEQ ID NO:23)
      MfeI

NA2R;
5'-tttgaattcatacatcgcatcgacaagg-3'    (SEQ ID NO:24)
      EcoRI
```

The reaction mixture comprised 10 ng microL of pJaL721 as template, 0.25 mM of dNTP, 100 pmol of each primer and 3.5 units of EXPAND™ polymerase in 100 microL of provided buffer with $MgCl_2$. The reaction was submitted to 94° C. for 2 minutes followed by 30 cycles of 92° C. for 1 min, 55° C. for 1 min and extension at 72° C. for 2 min. A final extension step at 72° C. for 10 minutes followed by a 4° C. hold step completed the program.

The 1.0 kb DNA fragment was gel-purified and ligated into a pT7Blue vector. The ligation mixture was transformed into E. coli JM109. The resulted plasmid (pHUda266) was sequenced. The amplified 1.0 kb fragment was confirmed that no changes had happen in the tandem NA2 promoter region with three extra amyR binding sites without leader sequences. The 1.0 kb DNA fragment having tandem NA2 promoter region with three extra amyR binding sites without leader sequences was obtained by EcoRI, MfeI digestion and ligated into an EcoRI site of pHUda263 with Ligation high. The ligated mixture was transformed into JM109. The resulted plasmid was pHUda267.

The 1.3 kb fragment of PME gene was excised from pt-vPME by BgI II and Xba I. It was ligated to pHUda267 cut by BamHI and XbaI. The resulting plasmid was termed pPME/267.

Example 19

Transformation of *Aspergillus niger* MBin19

Transformation of *Aspergillus niger* MBin119 can be achieved with general protoplasts methods. The preferred procedure for the invention is described below.

The host strain is propagated in 100 ml of non-selective YPG medium at 32□ C. for 16 hrs on a rotary shaker at 120 rpm. Cells are collected by filtering, washed with 0.6 M KCl and resuspended in 20 ml of 0.6 M KCl containing a commercial beta-glucanase product (GLUCANEX™, Novozymes A/S) at 600 microL/ml. The suspension is incubated at 32° C. at 80 rpm until protoplasts are formed, then washed twice with STC buffer. The protoplasts are counted with a hematometer and resuspended and adjusted in an 8:2:0.1 solution of STC:STPC:DMSO to a final concentration of $2.5 \times 10^7$ protoplasts/ml. About 3 microgram of DNA is added to 100 microL of protoplast suspension, mixed gently and incubated on ice for 20 min. One ml of SPTC is added and the protoplast suspension is incubated for 30 min at 37° C. After the addition of 10 ml of 50° C. Cove top agarose, the reaction is poured onto Cove-N agar plates and the plates are incubated at 32° C. for 5 days. As untransformed cells cannot grow on Cove-N medium, transformants are easily selected.

Example 20

Analysis of Transformants

The A. niger host strain MBin119 was transformed with the expression plasmid pPME/267 and selection positive transformants were isolated on Cove-N agar. Transformants were isolated on Cove-N2 agar and grown at 30° C. for 5 days and a piece of grown culture with agar was inoculated to 100 ml of MLC. After cultivation on a rotary shaker at 220 rpm at 30° C. for 2 day, 10 ml of each culture was transferred to 100 ml of GO-50 in shaking flask to cultivate at 30° C. for 5 days. Culture broth was centrifuged at 3500 rpm for 15 minutes and the supernatant was collected. The PME activity of the supernatant was determined as described below. PME hydrolyses pectin methyl ester under constant pH and temperature. The activity of PME is determined as the amount of titrant (0.050 N NaOH) consumed during neutralizing the liberated poly-galacturonic acid. Reaction mixture contains 0.48% (W/V) pectin and 10 mmol $Mg^{2+}$ (pH4.8). Reaction conditions are pH 4.8 and 30° C. One PEU (Pectin Esterase Unit) is the enzyme activity that produces one milli-acid equivalent per minute under the conditions. A transformant showed about 140 times higher yields than the parent A. niger strain used as a genomic DNA supplier (see Example 18).

What is claimed is:

1. A DNA sequence for regulating transcription of a structural gene encoding a polypeptide in a eukaryotic host cell comprising:
   (a) an NA2-tpi promoter comprising SEQ ID NO:1, and
   (b) one or more additional promoters with or without an mRNA initiation site, wherein the NA2-tpi promoter and the one or more additional promoters are operably linked to the structural gene.

2. The DNA sequence of claim 1, further comprising an RNA polymerase recognition site.

3. The DNA sequence of claim 2, wherein the RNA polymerase recognition site is a TATA box.

4. The DNA sequence of claim 1, wherein the one or more additional promoters are located upstream relative to the 5' end of the NA2-tpi promoter.

5. The DNA sequence of claim 4, wherein the one or more additional promoters and the NA2-tpi promoter are separated by from 0 to 100 bp of each other.

6. The DNA sequence of claim 5, wherein the one or more additional promoters and the NA2-tpi promoter are separated by from 10–50 bp of each other.

7. The DNA sequence of claim 5, wherein the one or more additional promoters and the NA2-tpi promoter are separated by from 4–30 bp of each other.

8. The DNA sequence of claim 1, wherein the eukaryotic host cell is a fungal host cell.

9. The DNA sequence of claim 8, wherein the fungal host cell is a filamentous fungal cell selected from the group consisting of *Aspergillus, Fusarium, Penicillium*, and *Trichoderma*.

10. The DNA sequence of claim 8, wherein the fungal host call is a yeast selected from the group consisting of *Hansenula, Pichia*, and *Saccharomyces*.

11. The DNA sequence of claim 1, wherein the structural gene encodes an enzyme selected from the group consisting of a hydrolase, Isomerase, ligase, lyase, oxidoreductase, and transferase.

12. The DNA sequence of claim 1, further comprising an RNA polymerase binding site with or without a region comprising an RNA polymerase recognition site and/or mRNA initiation site.

13. The DNA sequence of claim 1, wherein the 3' end of the one or more additional promoters is located upstream of the 5' end of the NA2-tpi promoter, which is located upstream of the structural gene.

14. The DNA sequence of claim 1, comprising two or more repetitive RNA polymerase binding sites.

15. The DNA sequence of claim 14, wherein there are 2–5 repetitive RNA polymerase binding sites.

16. The DNA sequence of claim 1, comprising two or three RNA polymerase binding sites wherein only the RNA polymerase binding she closest to the structural gene has an mRNA initiation site and optionally an RNA polymerase recognition site.

17. The DNA sequence of claim 12, wherein the region upstream to the region comprising the RNA polymerase recognition site and/or mRNA initiation site further comprises one or more transcription factor binding sites.

18. A DNA construct comprising a DNA sequence of claim 1 operative in a eukaryotic host cell and operably linked with the structural gene and a terminator region.

19. An expression vector comprising a DNA construct of claim 18 and a signal peptide-coding region.

20. A eukaryotic host cell comprising an expression vector of claim 19.

21. A method of producing a polypeptide, comprising:
   (a) cultivating the eukaryotic host cell of claim 20 in a nutrient medium suitable for production of the polypeptide; and
   (b) recovering the polypeptide.

22. The method of claim 21, wherein the polypeptide is native to the host cell.

23. The method of claim 21, wherein the polypeptide is heterologous to the host cell.

* * * * *